(12) United States Patent
Sinclair et al.

(10) Patent No.: US 8,397,592 B2
(45) Date of Patent: Mar. 19, 2013

(54) SYSTEMS AND METHODS FOR INLINE SAMPLING

(75) Inventors: James Sinclair, Carlsbad, CA (US); B. Albert Griffin, San Diego, CA (US); Minh Vuong, San Diego, CA (US)

(73) Assignee: Vertex Pharmaceuticals, Inc., Cambridge, MA (US)

( * ) Notice: Subject to any disclaimer, the term of this patent is extended or adjusted under 35 U.S.C. 154(b) by 398 days.

(21) Appl. No.: 12/709,414

(22) Filed: Feb. 19, 2010

(65) Prior Publication Data
US 2011/0203392 A1    Aug. 25, 2011

(51) Int. Cl.
*G01N 1/20* (2006.01)
(52) U.S. Cl. .................. 73/863.56; 73/32 R; 73/863.52
(58) Field of Classification Search ............... 73/863.41, 73/863.44, 863.45, 863.56, 863.52
See application file for complete search history.

(56) References Cited

U.S. PATENT DOCUMENTS

| 7,240,575 | B2 * | 7/2007 | Brone et al. | .................... 73/866 |
| 2008/0028872 | A1 * | 2/2008 | Brone et al. | ............... 73/863.21 |

FOREIGN PATENT DOCUMENTS
WO    WO 2008/080167 A2    7/2008

OTHER PUBLICATIONS

Prosys Sampling Systems Ltd.: 180 SAMPLER—Sampling Systems (retrieved from the Internet on Jan. 20, 2010 from http://www.prosysie/product/product2b_2a.html); 4 pages.

\* cited by examiner

*Primary Examiner* — Hezron E Williams
*Assistant Examiner* — Nashmiya Fayyaz
(74) *Attorney, Agent, or Firm* — Knobbe Martens Olson & Bear LLP (57) ABSTRACT

Methods and devices for inline sampling of a bulk material, such as a powder, are provided. The material's bulk density can be determined from samples drawn using methods and devices described herein. One embodiment of a method of sampling a material allows the material to flow through a sampling compartment, closes off the flow of material below the sampling compartment, builds up a column of material through the sampling compartment, shifts the sampling compartment to remove a slice of material in the column, and places the slice of material into a sample container. A device for sampling a material is provided in another embodiment. The device includes an inlet, an outlet aligned with the inlet, and a sample collector. The sample collector can include at least one through hole and be configured to move such that the at least one through hole can be moved into and out of alignment with the inlet and the outlet.

7 Claims, 10 Drawing Sheets

SYSTEMS AND METHODS FOR INLINE SAMPLING

BACKGROUND

1. Field of the Invention

The present invention relates generally to bulk density measurements and, more particularly, relates to systems and methods for sampling a bulk material, such as a powder, to measure its density.

2. Description of the Related Art

A process known as spray drying is used to manufacture a number of amorphous drug substances. In a conventional spray drying process, a compound is dissolved in an appropriate solvent and the resulting solution is atomized in a hot inert atmosphere that facilitates evaporation. As the solvent evaporates, the resulting particles drift downward, similar to snow, through a series of chambers and are eventually collected in a container. The container can include what is commonly referred to as an intermediate bulk container, or IBC.

In a variant of this process known as spray dried dispersion, a polymer is added to the solution so that the drug substance is embedded in a polymer matrix upon evaporation of the solvent. During the particles' descent through the series of chambers, their physical characteristics are sampled in various ways to assess their quality. For example, particle size can be measured by light scattering. Such online testing allows the plant operator to monitor the manufacturing in real time, or near real time, and thus ensure that the process is continuously within specification. Offline, batch testing of the same physical parameters does not allow for continuous adjustment of the process, and thus may result in entire batches being discarded because of insufficient quality. Parameters used to ensure the integrity of the manufacturing process are called commonly referred to as "Critical to Quality Attributes," or CQA.

In addition to particle size, another important CQA for spray drying is bulk density. Conventionally, bulk density is measured by scooping some powder out of the IBC, transferring the powder to a graduated cylinder, then weighing the powder and the cylinder. To obtain an accurate measurement, care must be taken not to cause tamping or settling of the powder. The density thus obtained is representative of the "bulk" material, that is, material that has not significantly settled under its own weight. The density of a solid material can be difficult to measure, depending on how its volume is defined. For example, gently pouring sand into a container will result in a lower density measurement than if the sand was compacted into the same container. The compacted sand will occupy less volume and thus exhibit a higher density. Powders and granular solids such as sand contain pockets of air in between individual grains. The density of the material including the air spaces is the bulk density, which differs significantly from the density of an individual granule or grain of the material with no air included.

Figure 1:
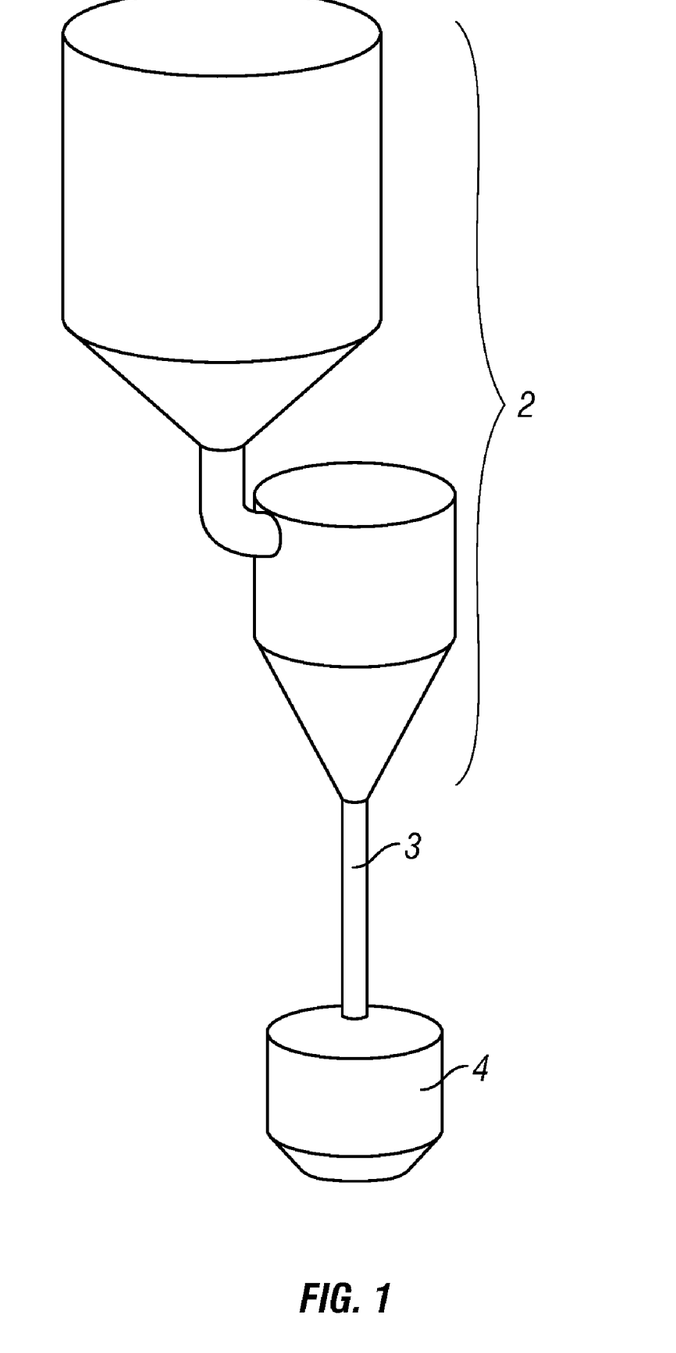
FIG. 1 is a perspective view of a spray drying system that can include a device for inline sampling of a bulk material.

The conventional method for measuring bulk density suffers significant drawbacks, however. With reference now to FIG. 1, a typical spray drying configuration includes one or more spray drying chambers 2, a chute 3, and a collection container 4. The chute 3 channels powder from the last spray drying chamber to the container 4. To sample material in a conventional spray drying system, a shutoff valve is closed to stop the flow of material into the container 4. The valve may include, for example, a butterfly valve disposed inside the chute 3 above the collection container 4. The container 4 is then disconnected from the chute 3 and wheeled away. After a second collection container 4 is wheeled into place and connected to the chute 3, the butterfly valve or other shutoff valve is reopened.

To collect a sample, an operator climbs onto a platform, reaches into the now-disconnected collection container 4, and removes material, such as a powder, from several locations to form an aggregate "sample." This sample is carefully transferred to a graduated cylinder for weighing. The entire process typically takes about fifteen minutes and involves moving heavy equipment. This process of collecting a sample requires a time consuming interruption to the spray drying process. Current methods also require the operator to scoop out some material from several locations in the container 4 to form an aggregate "sample," which may not be representative of the flow of material at any given moment. The current measurement process is thus cumbersome, time consuming, and imprecise.

Therefore, among other disadvantages, current designs cannot achieve accurate measurements with minimal movement of large, heavy containers and minimal interruption to the spray drying process. Thus, accurate, controlled, reliable, and reproducible bulk density sampling and measurement remains a significant challenge.

SUMMARY

The devices of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description," one will understand how the features of this invention provide several advantages over current designs.

In accordance with one aspect of the present invention, methods and devices are provided for inline sampling of a bulk material, such as a powder, to measure the material's bulk density. A method of sampling a material is provided in one embodiment. The method includes allowing the material to flow through a sampling compartment; closing off the flow of material below the sampling compartment; building up a column of material through the sampling compartment; shifting the sampling compartment to remove a slice of material in the column; and placing the slice of material into a sample container. The term "material" can include but is not limited to, an active pharmaceutical ingredient (API), chemical compound, dosage form, therapeutic agent, a drug formulating component (e.g., a component used as an ingredient in a pharmaceutical compound production/formulation process such as a filler, surfactant, polymer, lubricant, glidant, or disintegrant), and a mixture thereof. An example of the material can be the processed material that includes the compound provided as an example herein.

In another embodiment of a method of sampling a material, the method includes sampling the entire cross-sectional flow of a material through a passage; removing sampled material from the passage; and weighing the sampled material.

Another embodiment is a device for sampling a material. The device includes an inlet; an outlet aligned with the inlet; and a sample collector. The sample collector can include at least one through hole and be configured to move such that the at least one through hole can be moved into and out of alignment with the inlet and the outlet.

Yet another embodiment is directed to a device for sampling a material. The device includes a sample collecting element. The sample collecting element includes one or more passages, and is configured to enter and exit a flow path of the material such that the one or more passages enter and exit the flow path.

Further aspects, features and advantages of the present invention will become apparent from the detailed description that follows.

BRIEF DESCRIPTION OF THE DRAWINGS

These and other features, aspects, and advantages of the present invention will now be described in connection with embodiments of the present invention, in reference to the accompanying drawings. The illustrated embodiments, however, are merely examples and are not intended to limit the invention.

DETAILED DESCRIPTION

The following detailed description is directed to certain specific embodiments of the invention. However, the invention can be embodied in a multitude of different ways as defined and covered by the claims. In this description, reference is made to the drawings wherein like parts are designated with like numerals throughout.

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages, or features will be embodied in any particular embodiment of the present invention.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Figure 2:
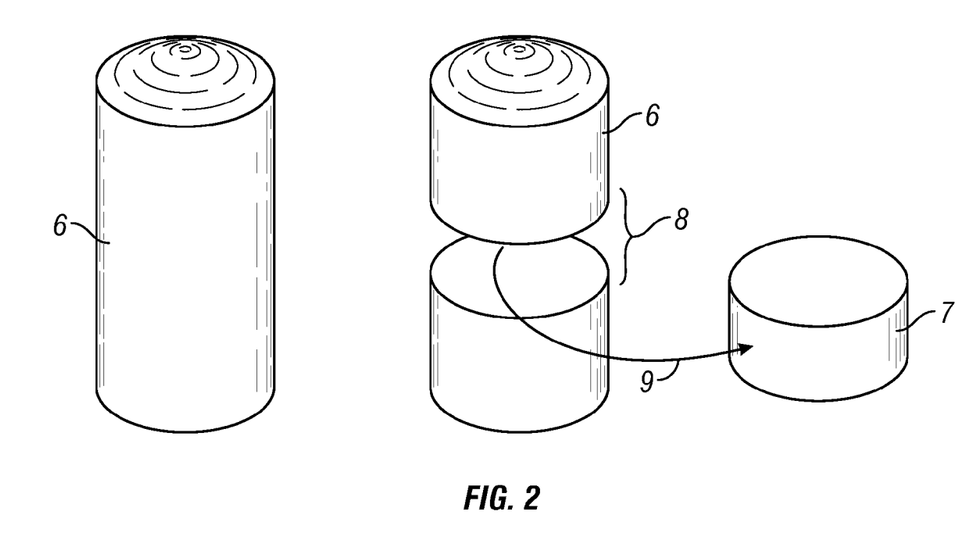
FIG. 2 is an illustration of a method of taking an inline sample of a material according to one embodiment of the present invention.

FIG. 2 generally illustrates a method to take an inline sample of a material, such as a powder, in accordance with one embodiment of the invention. In this embodiment, the flow of material is temporarily stopped above the collection container 4. The flow of material can be stopped, for example, by closing a butterfly valve located in the chute 3. As a result, the material accumulates and builds up into a column of material 6 in the chute above the closed valve. After a column of appropriate height is achieved, a fixed volume of material 7 is removed from the column 6 at a collection point 8. Arrow 9 illustrates the removal of the slice of material 7 from the column 6. As soon as the fixed volume of material is removed, the flow of material into the container can be restored, such as, for example, by opening the butterfly valve. The fixed volume of material 7 can then be weighed offline, without affecting or disturbing the continued flow of material into the container 4.

Figure 3:
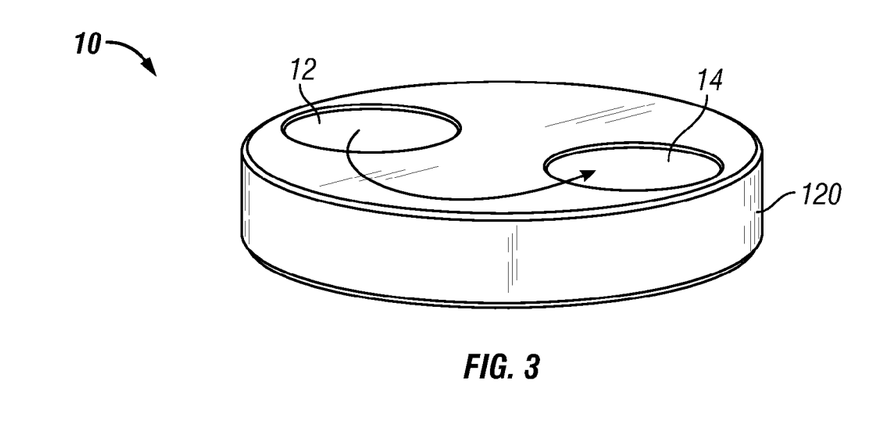
FIG. 3 is a perspective view of an embodiment of a sample collecting element of a device for inline sampling of a bulk material.

FIG. 3 illustrates one embodiment of a sample collecting element or sample collector 10 configured to accomplish a method such as that illustrated in FIG. 2. The sample collecting element 10 can comprise a disc 120. The disc 120 includes one or more through holes or sampling compartments 12. In the embodiment illustrated in FIG. 3, for example, the disc 120 comprises two sampling compartments 12, 14. The disc 120 can be located between the last spray drying chamber 2 (FIG. 1) and above the collection container 4 (FIG. 1). The disc 120 can be aligned, for example, such that the sampling compartment 12 is in line with the chute 3 (FIG. 1) at the start of the sampling method. Thus, when sampling operations are not occurring, the disc 120 can be situated in the flow of material such that material flows unimpeded from the spray drying chambers 2, into the chute 3, through the sampling compartment 12 of the disc 120, and into the collection container 4.

Figure 4:
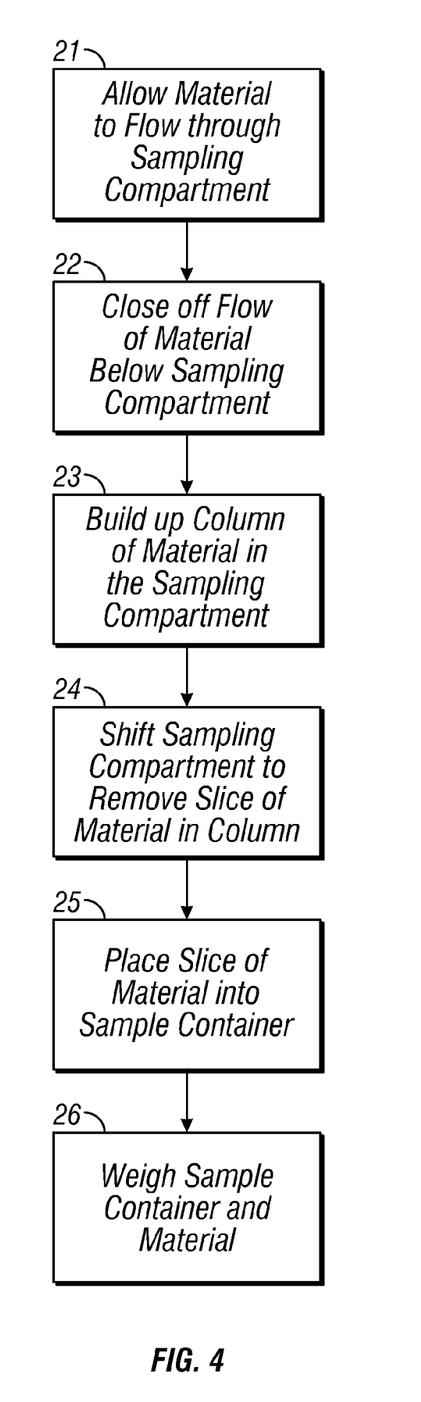
FIG. 4 is a flowchart illustrating one embodiment of a method for collecting a sample of material using the sample collecting element of FIG. 3.

FIG. 4 is a flowchart illustrating in greater detail one embodiment of the method for collecting a sample of material, such as a powder or other bulk material. With reference now to FIGS. 2, 3, and 4, the method begins at block 21 in which material is allowed to flow from the final spray drying chamber 2, into the chute 3, through the sampling compartment 12 of the disc 120, to a collection container 4. Moving to a block 22, the flow of material below the sampling compartment 12 is closed off. As described above, the flow of material can be stopped by closing a butterfly or other shutoff valve located above the collection container 4 and below the disc 120. Moving next to a block 23, a column of material 6 builds up above the shutoff valve. Specifically, the column of material 6 builds up inside the chute 3, including that part of the chute 3 formed by the sampling compartment 12 of the disc 120. In one embodiment, the shutoff valve remains closed long enough to allow accumulation of material in the space between the shutoff valve and the disc 120, through the sampling compartment 12, and into the chute 3 above the sampling compartment 12.

The method next moves to a block 24, in which the sampling compartment 12 is shifted to remove a slice of material 7 in the column 6. In one embodiment of the method, the disc 120 is rotated in the direction of arrow 9 to remove a portion of material 7 from the column 6. In one embodiment, the disc 120 is rotated 180° to remove the sample from the column 6, such that the sampling compartment 14 is aligned with the chute 3 at the end of the disc's 180° turn.

The shutoff valve can be opened after the material 7 is removed from the column 6, once again allowing material to flow unimpeded through the chute 3, now falling through the sampling compartment 14, to the container 4. Thus, the flow of material through the spray drying system can be reopened almost immediately after material is removed from the column 6 at block 24. It will be appreciated, however, that the valve can be reopened later in the process.

Moving next to a block 25, the slice of material 7 is placed inside a sample container. In one embodiment, for example, a sample container is disposed below the disc 120 and configured to accept a material sample that drops out of the sample compartment 12 when the disc 120 is shifted or rotated a full 180° and becomes aligned with the sample container.

At block 26, the sample container and material are weighed to obtain a bulk density measurement of the material. Specifically, the volume of the slice of material 7 and the weight of the sample container can be calculated with precision. The weight of the material sample is calculated by subtracting the tare weight of the sample container from the total weight of the sample container and the material. The bulk density of the material can then be calculated by dividing the weight of the sample by the known volume of the sampling compartment 12.

Other configurations of the sample element 10 and other methods of removing material from the column 6 are possible. For example, in one embodiment, in lieu of rotating a disc, a linear element is pushed through the column 6 to remove a slice of material 7. In another embodiment, the disc 120 comprises one sampling compartment 12. The disc 120 is first rotated 180°, at which point the slice of material captured in the sampling compartment 12 is placed in a sample container. As described above, the sample container may be located below the disc 120 and configured to accept the material sample when the sample compartment rotates 180° and is aligned with the sample container. The disc 120 is then rotated another 180° to return the sampling compartment to its original position in alignment with the chute 3. When the stop valve is reopened, the chute 3, aligned with the sampling compartment 12, again allows unimpeded passage of the material to the collection container 4.

As illustrated in FIGS. 2 and 3, the method captures and removes an entire cross-sectional slice of column 6, thus providing a complete and representative sample of the material for accurate, reproducible measurements. Embodiments of the method described herein result in accurate bulk density measurements for several reasons. The methods described herein avoid the problems associated with inserting a relatively small cup or other collection device into the material flow path, allowing the cup to fill with material, and then removing the cup from the flow path. By introducing a small cup or other device into the flow of material in order to collect and measure the density of the material, these methods may introduce sampling errors into the measurement. For example, the presence of the cup or other device in the material flow path may cause vortices or other disturbances in the flow that can affect the quantity and distribution of material that is collected in the cup. In addition, the material may not be falling with the same mass flow across its entire cross section, and a small cup will often fail to produce a truly representative collection of material. Embodiments of the inline sampling method described herein advantageously avoid such sources of sampling error by allowing the material to fall, undisturbed, into a column, then quickly and efficiently removing a portion of that column for measurement.

One embodiment of a device 100 for inline sampling of a bulk material in accordance with the method will now be described in greater detail with reference to FIGS. 5-9. FIG. 5 is a perspective view of the exterior of the device 100. FIG. 6 is a perspective view of a cross-section of the device 100 taken along line A-A of FIG. 5, the device shown in a "closed flow" configuration. FIG. 7 is a plan view of the cross-section of the device 100 illustrated in FIG. 6, the device shown in an "open flow" configuration. FIG. 8 is an exploded view of the device 100 illustrated in FIGS. 5-7. FIG. 9 is a detailed view of a turning mechanism of the device 100.

As described in greater detail above with reference to FIGS. 2-4, the device 100 can be placed inline with the flow path of material in a spray drying system. For example, the device 100 can be positioned along or within a chute 3 (FIG. 1) between a spray drying chamber 2 and a collection container 4. The device 100 can include a disc 120 to capture and measure an inline sample of the material as it travels from the last spray drying chamber 2 to a collection container 4.

The device 100 includes a top plate 115, a disc 120, a ring 125, and a bottom plate 130. The top plate 115, the ring 125, and the bottom plate 130 are configured to enclose the disc 120 such that in can rotate within the device 100. The device 100 can also include a ratchet 210, or other suitable mechanism, to rotate the disc 120 within the device 100, thus removing a slice of material 7 (FIG. 2) from a column 6. Various clamps and seals, described in greater detail below with reference to FIG. 10, may also be provided to connect and create seals between the components of the device 100.

The disc 120 can include two through holes or sampling compartments 12, 14. The sampling compartments 12, 14 are disposed 180° apart in the disc 120 according to one embodiment. As described in greater detail above with reference to FIG. 2-4, some embodiments of the disc 120 only include one sampling compartment 12. Thus, persons of skill in the art will understand that one, two, three or more sampling compartments can be provided in the disc 120. In embodiments comprising three compartments, the compartments can be located, for example, 120° apart in the disc 120.

The top plate 115 can include an inlet opening 105. The top plate 115 may optionally have indentations 140 or other features to facilitate positioning of seals or clamps, assist movement of the ratchet 210, or reduce the amount of material used to construct top plate 115. Although not shown in FIGS. 5-8, the top plate 115 can also comprise additional inlets or portals to facilitate a sampling process. For example, in one embodiment the top plate 115 optionally comprises a vent 142, described in greater detail below.

The bottom plate 130 includes two outlets 145, 150 according to one embodiment. The inlet 105, the sampling compartments 12, 14, and the outlets 145, 150 can have the same or substantially similar diameters. As illustrated in FIGS. 6-7, the inlet 105, the outlet 145, and one of the sampling compartments 12, 14 can be aligned to form a passage 155. The device 100 can be disposed in a chute 3 (FIG. 1) such that material, such as a powder, flowing from a spray drying chamber 2 and into the chute 3 flows through the passage 155 before being collected in a collection container 4.

The device 100 can be coupled to a chute 3 (FIG. 1) via an inlet coupler 165 configured to feed powder into the device 100. For example, a conventional spray drying devices may connect the spray drying chamber 2 to a collection container 4 using a chute 3 having a 6-inch diameter. According to some embodiments, the inlet 105 of the top plate 115 has a 4-inch diameter. An inlet coupler 165 having a 6-inch diameter at one end and a 4-inch diameter at the other end can thus be configured to couple a 6-inch diameter chute 3 to a 4-inch diameter inlet 105. Persons of skill in the art will understand that the inlet 105 may have a 6-inch diameter, such that the chute 3 can be connected directly to the device 100 or indirectly via an inlet coupler 165 of constant 6-inch diameter.

The device 100 can be coupled to a chute 3 or a collection container 4 (FIG. 1) disposed below the device 100 via an outlet coupler 170. Like the inlet coupler 165, the outlet coupler 170 may vary in diameter to connect an outlet 145 having a 4-inch diameter to a chute 3 having a 6-inch diameter.

Figure 6:
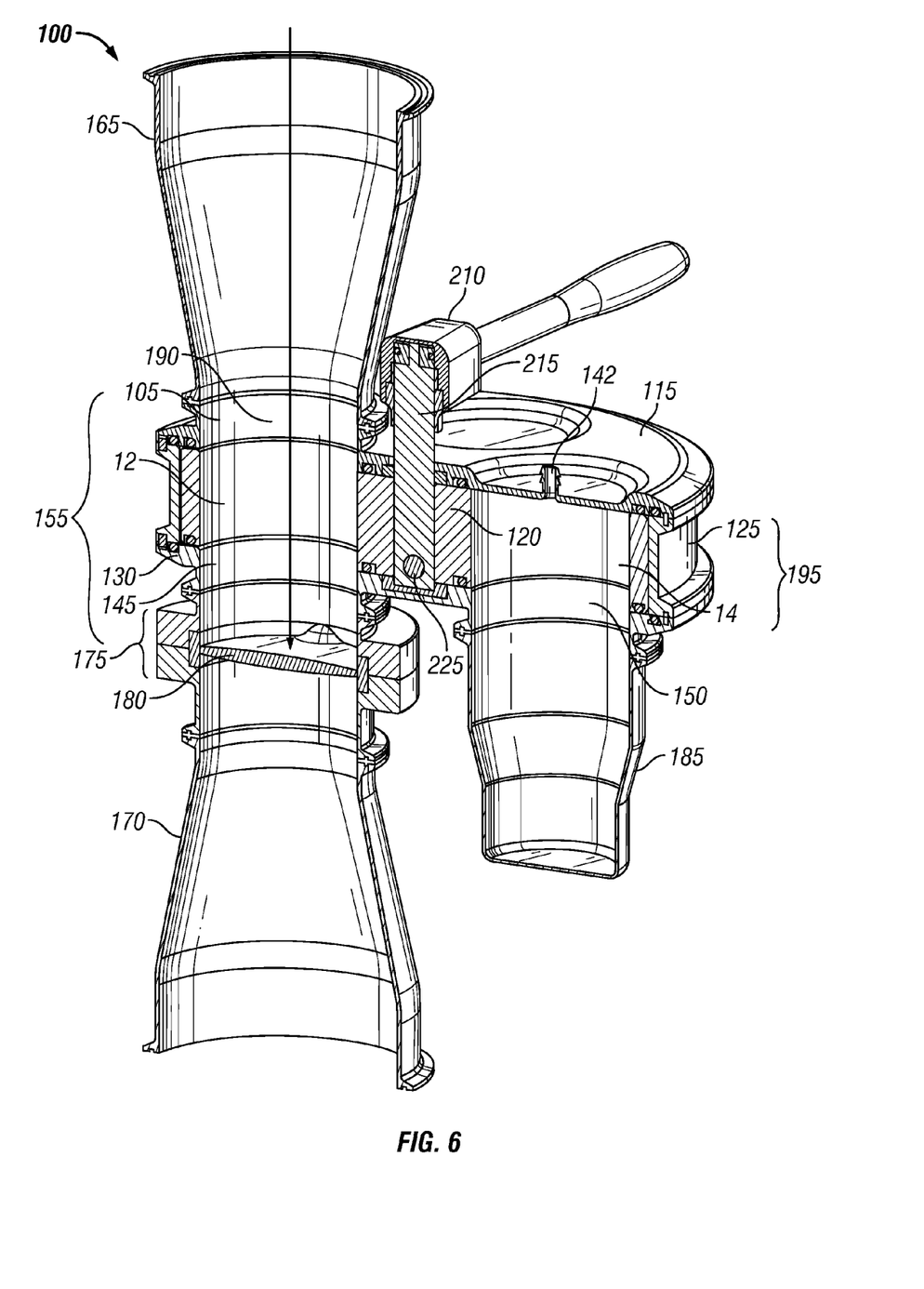
FIG. 6 is a cross-sectional view of the device illustrated in FIG. 5, shown with a closed valve.
Figure 7:
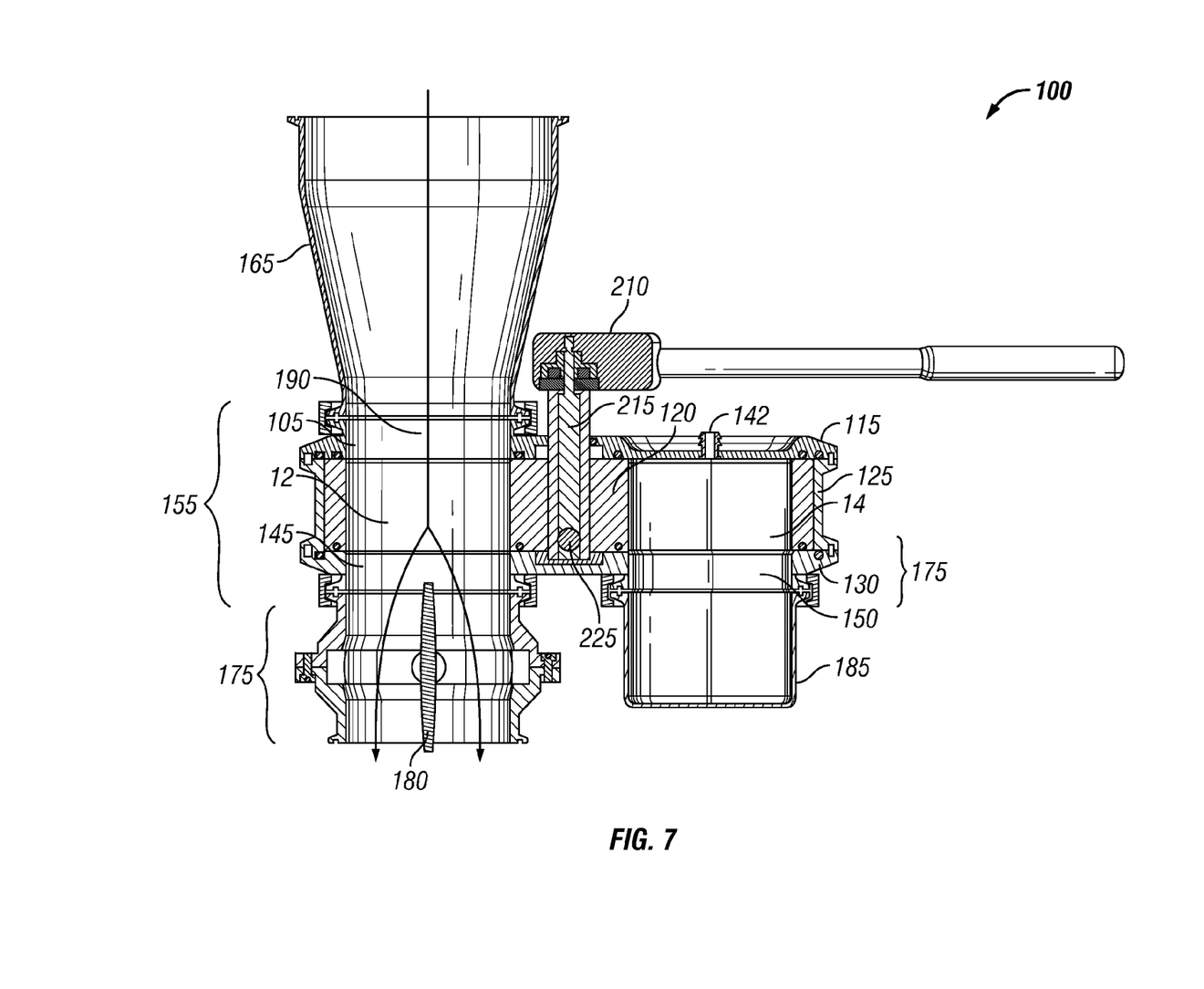
FIG. 7 is a cross-sectional view of the device illustrated in FIG. 5, shown with an open valve.

According to some embodiments, the device 100 is connected to the outlet coupler 170 via a valve assembly 175. In one embodiment, the valve assembly 175 includes a butterfly valve 180 that can be positioned horizontally in the passage 155 to close off the flow of material through the passage 155 (FIG. 6). Alternatively, the butterfly valve 180 can be positioned vertically to allow material to flow unimpeded through the passage 155 (FIG. 7). Persons of skill in the art will understand that other means to close off the flow of material through the passage 155 are possible, such as but not limited to a ball valve, a gate valve, a globe valve, or a thin disc located below the disc 120. Other embodiments of the present invention, such as one described below with reference to FIG. 12, include other methods and devices to stop the flow of material through the passage 155.

Additionally, the device 100 can include a sample container 185 configured to mate with another outlet 150 of the bottom plate 130.

The device 100 can accomplish the method described above with reference to FIGS. 2-4 as follows. The disc 120 is positioned between the top plate 115 and the bottom plate 130 such that the sampling compartment 12 is aligned in the passage 155 formed between the inlet 105 and the outlet 145. As illustrated in FIG. 7, the butterfly valve 180 is initially in a vertical, or "open flow" configuration. In this configuration, material flows into the device 100 from the chute 3 via the inlet coupler 165. The material then travels through the inlet 105, into the passage 155, and through the sampling compartment 12. The material then flows out the outlet 145, through the outlet coupler 170 and past the open valve assembly 175 to a collection container 4 disposed below the device 100.

To begin a sampling operation, the device 100 is changed to a "closed flow" configuration in which the butterfly valve 180 is rotated to a horizontal position within the valve assembly 175. Material flowing through the device 100 begins to accumulate inside the passage 155 above the butterfly valve 180. As material accumulates, a column of powder is formed inside the passage 155, eventually filling the sampling compartment 12. In some embodiments, material is allowed to fill the passage 155 past the top of the sampling compartment 12, into a cavity 190 located inside the inlet 105 of the top plate 115. The amount of time it will take to fill the passage 155 past the sampling compartment 12 can be determined based on the flow rate of the material through the spray drying system. Various sensors or windows could be provided to detect the level of powder in the column as well, although care must be taken that the materials used for these features don't contaminate or otherwise negatively affect the flowing material, especially in a chemical or drug production environment.

When the material has accumulated to a point in the passage 155 above the sampling compartment 12, the disc 120 can be rotated 180° using a turning mechanism. In one embodiment, the turning mechanism comprises a ratchet 210 coupled to the disc 120 via a post 215. Operation of the ratchet 210 to turn the disc 120 is described in greater detail below with reference to FIG. 9. It will be understood that the ratchet 210 or other turning mechanism can be configured to rotate the disc 120° (in the case of a disc 120 configured with three sampling compartments, for example), or other amounts.

When the disc 120 is rotated 180° as described above, the rotational motion of the disc 120 removes a slice of material 7 (FIG. 1) from the column 6 that has accumulated in the passage 155. Advantageously, excess material located above the sampling compartment 12 is not transported with the slice of material 7 because the rotation of the disc 120 pushes just the contents of the sampling compartment 12 out of the column 6. In some embodiments, o-ring or other seals on the disc 120 or the top plate 115 assist in limiting the volume of transported material to just that material located inside the sampling compartment 12.

As the disc continues it rotation through 180°, the slice of material 7 is transported by the sampling compartment 12 from its initial first location in the passage 155, through the device 100, to a second location within the device 100. When the disc 120 completes its 180° turn, the sampling compartment 12, and the slice of material 7 (hereinafter "material sample 7"), are aligned with the outlet 150 in the bottom plate 130. This alignment creates a new passage 195 which allows the material sample 7 to flow from the sampling compartment 12 to the sample container 185.

Thus, all or substantially all of the material sample 7 from the sampling compartment 12 is moved and placed in the sample container 185 when the disc 120 is rotated a full 180°. Simultaneous with this shift of the material sample 7 within the device 100, the sampling compartment 14 is moved from its initial location above the sample container 185 to a second location in alignment with the inlet 105 and the outlet 145, thus creating a new passage 155 for the flow of material. The device 100 can then be returned to an "open flow" configuration by opening the butterfly valve 180 to a vertical position, thus allowing the remainder of the column of material 6 to flow through the passage and into the collection container 4.

The sample container 185 can be disconnected from the device 100 after the material sample 7 is placed in the container. The sample container and material sample can then be weighed to determine the bulk density of the material, as explained in greater detail above with reference to FIGS. 2-4. In some spray drying systems, material flows through the device 100 at a pressure greater than ambient pressure. Thus, a vent 142 may be optionally provided in the top plate 115 to relieve pressure in the device 100 before the sample container 185 is removed from the bottom plate 130. The vent 142 can be used to equalize the pressure in the device 100 to ambient pressure before disconnecting the sample container 185 for weighing.

Components of the device 100 can be made of any suitable material, including plastic or metal. In one embodiment, the top plate 115, the ring 125, and the bottom plate 130 are made of stainless steel. In another embodiment, these components are made of a polished hard metal, such as titanium. The disc 120 can be made of metal, such as stainless steel or a metal alloy such as HASTELLOY® by Haynes International, Inc. The disc 120 can also be made of plastic, such as polytetrafluoroethylene (PTFE), such as TEFLON® by DuPont, polyether ether ketone (PEEK), or polyoxymethylene, such as DELRIN® by DuPont.

FIG. 9 is an illustration of one embodiment of a turning mechanism of the device 100. The turning mechanism includes a ratchet 210 with a lever 220 coupled to one end of a post 215. The other end of the post 215 may be coupled to the disc 120 by a dowel 225 (FIGS. 6-8). In one embodiment, the turning mechanism is configured to allow the disc 120 to turn only in the clockwise direction.

Figure 9:
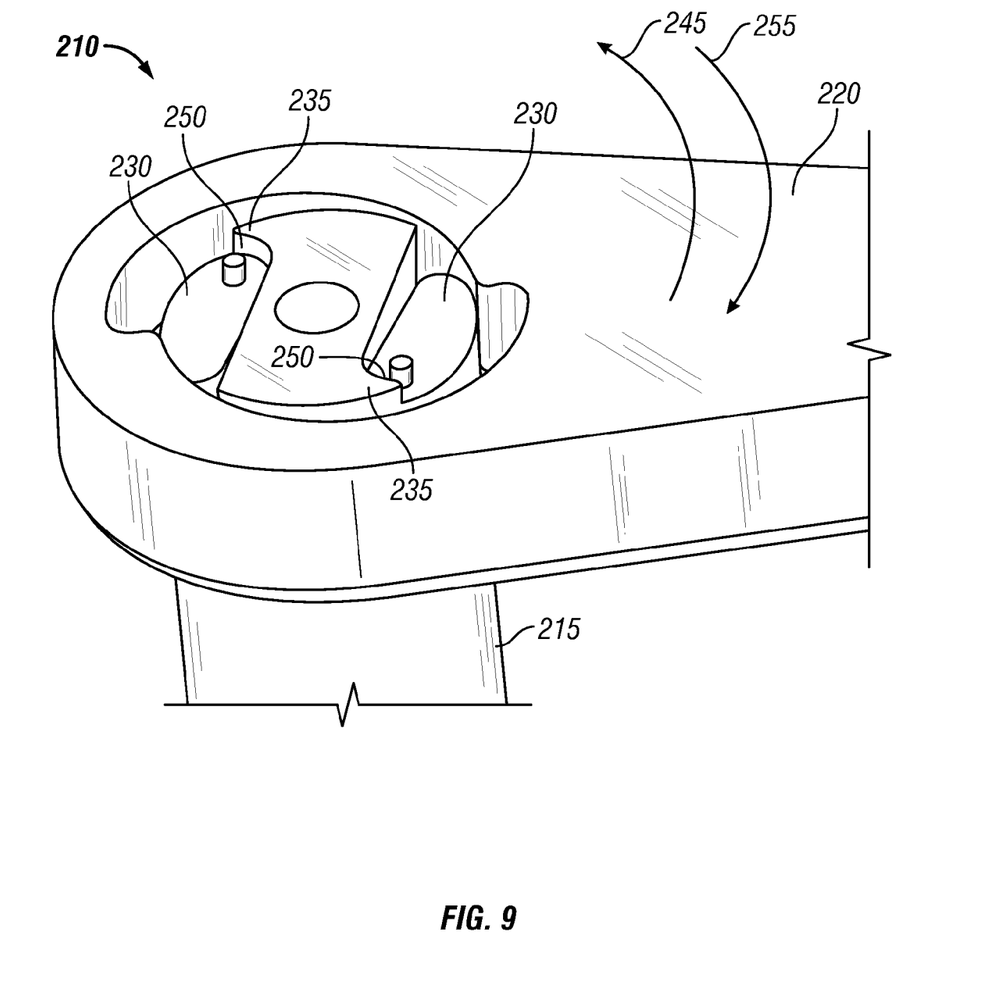
FIG. 9 is a perspective view of a turning mechanism of the device illustrated FIG. 5.

The lever 220 includes two spring loaded pawls 230 which can engage teeth 235 on the post 215. The ratchet cycle is 180° according to some embodiments. To operate the ratchet 210 and turn the disc 120 within the device 100, the lever 220 is first located against a stop 240 located on the top plate 115. The lever is then rotated counterclockwise in the direction of arrow 245. This rotation causes the pawls 230 to spring into recesses 250 on the post 215. The user may determine that the lever 220 and the post 215 are locked together by, for example, hearing the pawls 230 click into the recesses 250. In some embodiments, the user can determine that the lever 220 and the post 215 are locked together by the location of the lever 220 in a position 180° away from the stop 240.

The lever 220 is then turned clockwise in the direction of arrow 255. The clockwise rotation of the pawls 230 against the teeth 235 causes the post 215 to also rotate clockwise in a clockwise direction. In one embodiment, the lever 220 can only be turned 180°, until it reaches the stop 240. The stop 240 can prevent the disc 120 from rotating more than 180°, thus ensuring correct alignment of the sampling compartments 12, 14, with the inlet of the top plate and the outlets of the bottom plate. To rotate the disc 120 another 180°, the lever 220 is again turned counterclockwise 180° until the pawls 230 lock with the teeth 235 of the post 215. In this manner, the disc 120 can only be turned in a clockwise direction. In other embodiments, the turning mechanism does not include a ratchet 210 and the disc 120 can be rotated in either the clockwise or counterclockwise directions. In yet another embodiment, a gear box is used to reduce the torque required to turn the lever 220.

Persons of skill in the art will understand that embodiments of the device 100 can be implemented on different scales. For example, the device 100 can be scaled up or down to accommodate a disc 120 that is several inches to several feet in diameter with a variety of thicknesses.

Figure 10:
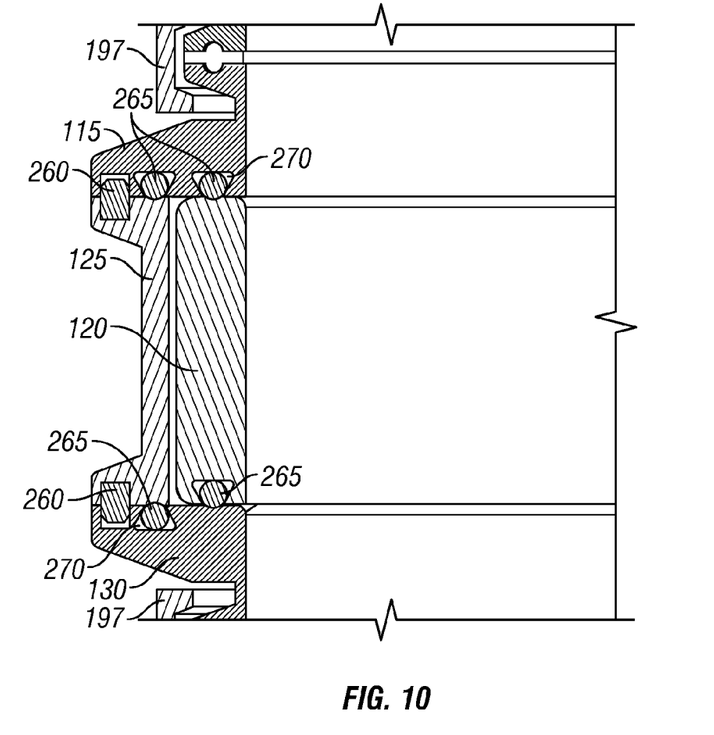
FIG. 10 is a cross-sectional view of a top plate, a disc, a ring, and a bottom plate of the device illustrated in FIG. 5.

FIG. 10 is a close-up cross-sectional view of the top plate 115, the disc 120, the ring 125, and the bottom plate 130 according to one embodiment of device 100. Various brackets and clamps can be used to connect the top plate 115, the ring 125, and the bottom plate 130 to form an enclosure around the disc 120. In some embodiments, the top plate 115, the ring 125, and the bottom plate 130 create an airtight enclosure around the disc 120. The enclosure can prevent material flowing through the device 100, such as a powder, from escaping the device between the plates and the ring. In one embodiment, locating dowel pins 260 are provided to assist assembly of the ring 125, the top plate 115, and the bottom plate 130. The pins 260 can ensure the plates are properly oriented with the ring 125 to create an enclosure, as well as ensure the inlet 105 is properly aligned with the outlet 145 to create the passage 155.

In some aspects, triclamps 197 (FIGS. 7-8, 10) are provided to connect and/or seal the inlet coupler 165, the valve assembly 175, and the sample container 185 to the device 100. Triclamps (not shown in the figures) can also be used to clamp the top and bottom plates to the ring. The triclamps 197 can be configured to prevent material from escaping the device at these connections and to facilitate disassembly and reassembly of the device 100. It will be understood that the device 100 can comprise other fasteners in lieu of or in addition to triclamps, such as nuts and bolts. Brackets and clamps can be made of any suitable material, including plastic or a metal, such as stainless steel.

Figure 8:
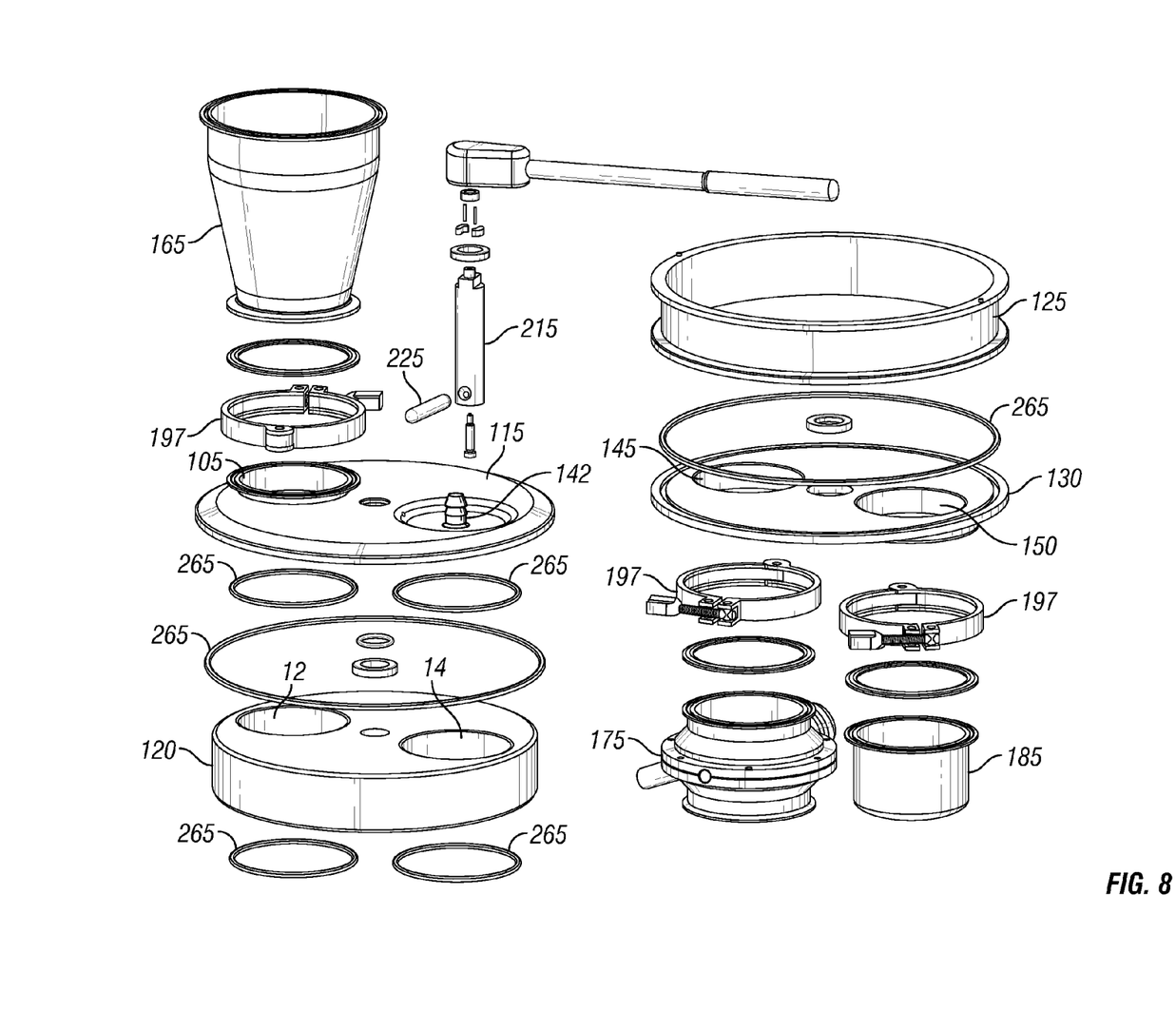
FIG. 8 is an exploded perspective view of the device illustrated in FIG. 5.

The device 100 can also include seals configured to prevent material from escaping the device at certain locations. As illustrated in FIGS. 8 and 10, for example, the disc 120, the top plate 115, and the bottom plate 130 can comprise one or more seals 265, which may comprise o-rings, spring energized seals, or the like. In some embodiments, the seals 265 are Teflon-encapsulated O-rings. However, the seals may comprise any suitable material, such as silicone, nitrile, or VITON® by DuPont. In certain aspects, the seals 265 are housed in dovetail grooves 270 to ensure the seals 265 remain in place during assembly of the device 100. Persons of skill in the art will understand that the device 100 can include rectangular-shaped grooves instead of dovetail grooves.

Figure 11:
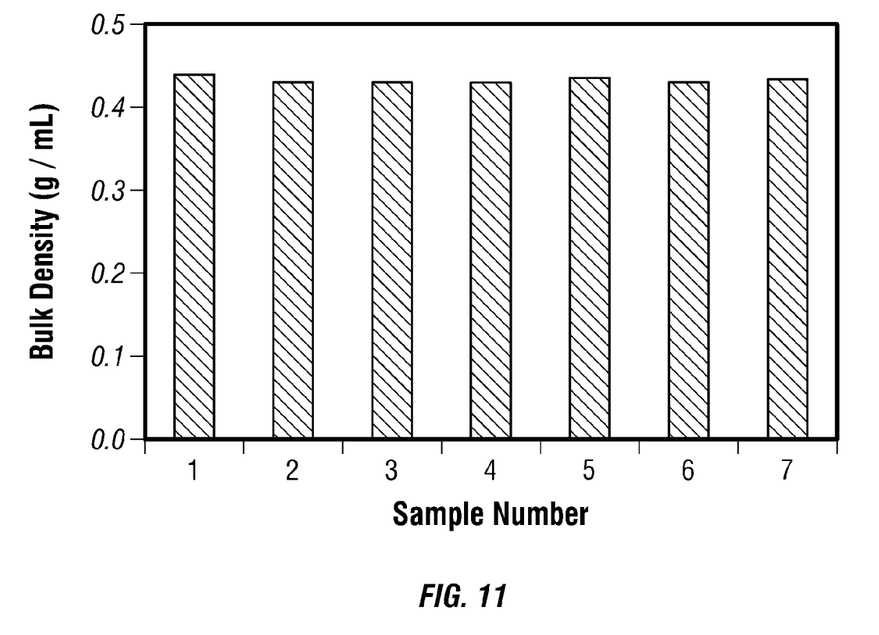
FIG. 11 is a graph of sampling data obtained with an embodiment of the device illustrated in FIG. 5.

FIG. 11 illustrates sampling data obtained with an embodiment of the device 100. As discussed in greater detail above, current methods to sample a material in a spray drying system require an operator to scoop material from three locations within a collection container into a measurement device, such as a graduated cylinder. The material sample is handled several times during the collection and measurement process, which may cause settling of the material in the measurement device. Uncontrolled and unpredictable settling of the material in this manner can introduce a significant source of error in the bulk density computation. Furthermore, current methods attempt to approximate sampling an entire cross section of the material flow by taking material from multiple locations within the collection container, but such methods add complexity and introduce error into the process. Additionally, measurement errors are also introduced when the volume of a material is read from a graduated cylinder. In contrast, methods and systems described herein sample an entire cross-section of the material flow to acquire a sample of well-defined volume. The material sample can be quickly and efficiently transferred to a sample container without handling by an operator. This eliminates the need for extra care in handling the sample container to minimize tamping or settling of the material in the container. Further, methods and systems herein do not measure volume by reading a graduated cylinder, and instead use a fixed, known volume of a sampling compartment in the disc 120 to determine the material sample's volume. As a result, the method and embodiments of devices described herein that implement the method can result in very accurate, repeatable bulk density measurements.

For example, in one experiment an embodiment of a device 100 was tested using a chemical compound in spray dried dispersion form. The chemical name of the compound used in the test is (1S,3aR,6aS)-2-[(2S)-2-[[(2S)-2-cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide (hereinafter "Compound 1"). Use of Compound 1 in a spray-drying procedure is exemplified in International Publication No. WO 2008/080167 (which corresponds to International Application No. PCT/US2007/088837), the entire contents of which is incorporated herein by reference.

During the test process, a commercial powder feeder fed Compound 1 through a screen sieve. Compound 1 then flowed through a six-inch powder chute, through an embodiment of the device 100 within the powder chute, and into a collection container. The Compound 1 material was sampled seven times from the test apparatus. The bulk density of each sample was measured according to the method described herein. The results of this experiment are illustrated in FIG. 11. For these seven samples, the mean bulk density is 0.4325 g/mL and the coefficient of variation (standard deviation/mean) is 0.9%. This repeatability and accuracy of sample measurements using the methods 20 and embodiments of the device 100 can be two to three times better than those obtained by current sampling methods.

Methods and systems described herein can also significantly reduce sampling times. Because the device 100 and the method use an inline design, an operator need not disconnect and move a collection container in order to access and sample a material in the container. In some embodiments, material flow is only interrupted during the time period it takes to overfill the sample compartment 12. Depending on the flow rate of the material through the device 100, the flow of material through the device 100 may only be stopped for approximately one minute. In contrast, current methods may interrupt flow of the material for around six minutes while one collection container is disconnected, removed, and replaced with a new collection container.

Figure 12:
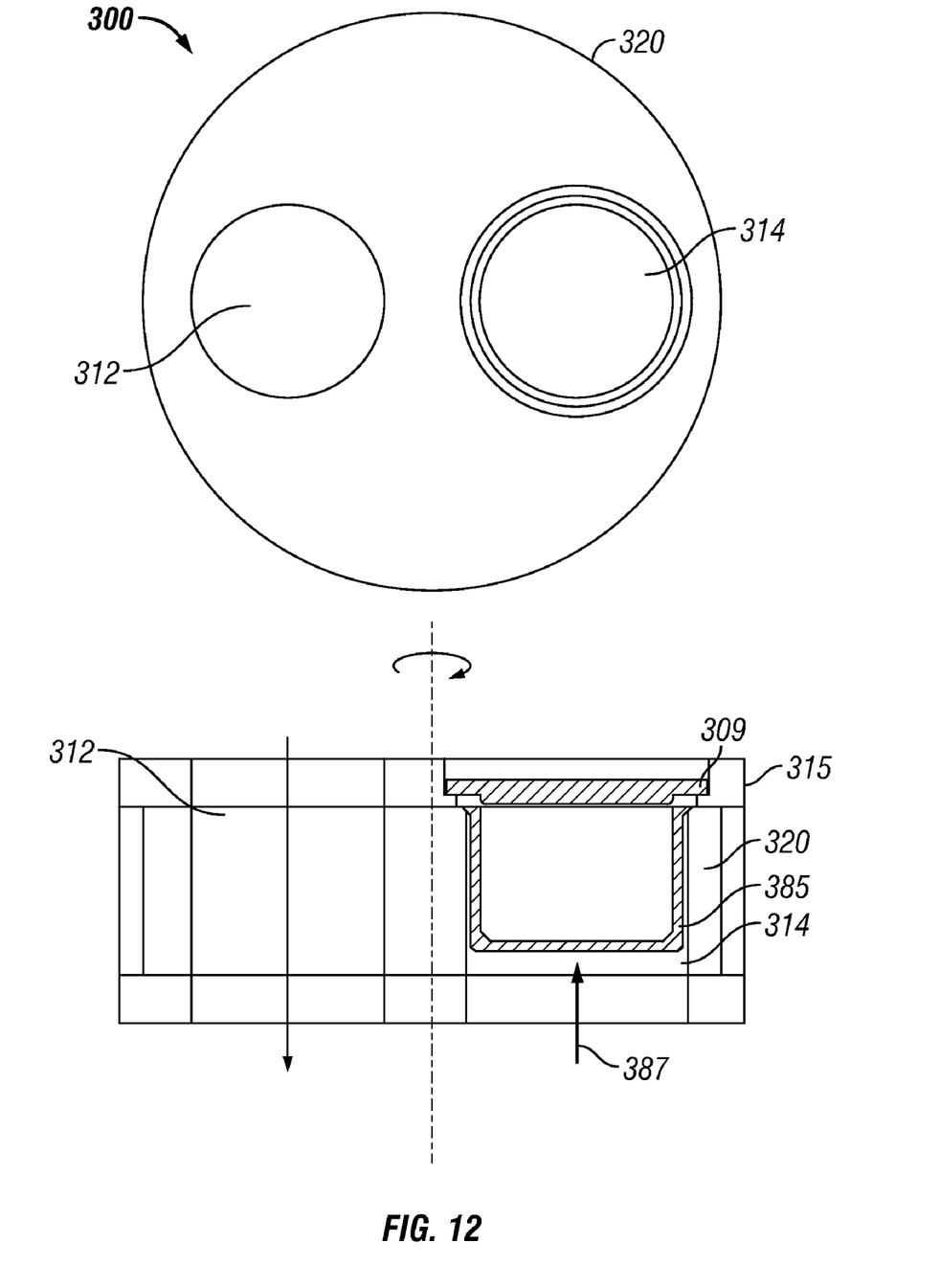
FIG. 12 is top plan view and a cross-sectional view of another embodiment of a device for inline sampling of a bulk material.

Another device 300 for implementing the method will now be described with reference to FIG. 12. FIG. 12 illustrates top plan and cross-sectional views of a disc 320 configured to rotate inside a device 300. The disc 320 includes two through holes 312, 314. The through holes 312, 314 are disposed 180° apart in the disc 320. In one embodiment, the through hole 312 is aligned in a passage 355 as described in greater detail above with reference to FIGS. 5-8. The through hole 314 is configured to accept a sample container 385. In some aspects, the cross-section of the sample container 385 is nearly identical to the cross-section of the through hole 312, preferably taking up 95% or more of the cross section of the through hole.

The device 300 can include a top plate 315 with two openings 305 and 307. The opening 307 can house a lid 309 which is configured to close and/or or seal the sample container 385. The device can also include a bottom plate 330 with two openings 310, 350.

To operate the device 300, the opening 305 of the top plate 315, the through hole 312, and the opening 310 on the bottom plate 330 are aligned to form a passage 355 for the flow of material through the device 300. The disc 320 can then be rotated 180° by a turning mechanism, such as the ratcheted lever 220 described above (FIG. 9), to bring the sample container 385 into the passage 355. The flow of material into the device 300 is now interrupted, such that material begins to accumulate in the sample container 385. The sample container 385 can remain in the passage 355 until material has accumulated to a level above the sample container 385.

The disc 320 can then be rotated another 180°. As a result of this rotation, excess powder above the sampling container 385 is retained in the cavity 190 and the through hole 312 is again aligned with the openings 305, 310 to form a passage 355 for the flow of material through the device 300. The material-filled sample container 385 is removed from the flowpath by the rotation of the disc 320, and can now be removed from the disc 320. In one embodiment, the sample container 385 is removed by pushing up on the sample container 385 through the opening 350 in the bottom plate 330, in the direction of arrow 387. As the sample container 385 rises out of the disc 320, it can catch the lid 309 disposed in the top plate 315. The lid 309 can be configured to prevent material from being spilled out of the sample container 385 as it is removed and handled for weighing. The lid 309 can also prevent exposure of the material sample to the ambient air. The lid 309, the sample container 385, and the material sample are then weighed, as described above, to determine the bulk density of the material sample.

It will be understood that spray drying systems using embodiments of the device 300 need not use a butterfly or other valve to stop the flow of material below the disc 320. This is because introduction of the sample container 385 into the passage 385 is sufficient to cause material to accumulate in the sample container 385. Elimination of the butterfly valve from the spray drying system can advantageously reduce the risk of bridging, in which material accumulates on or around the open butterfly valve and causes interruptions to the flow of material past the valve. In addition, the amount of time material flow is interrupted to collect a sample can be minimal, as the flow need only be interrupted to fill the volume of the sample container 385.

In addition, methods described herein can include weighing the material sample in situ within the device 100. In one embodiment, for example, the slice of material 7 (FIG. 1) that is removed from the column 7 is placed on a weighing surface of a piezoelectric scale located below the device 100. The slice of material 7 rests on the weighing surface, a weight measurement is obtained, and then the slice of material 7 is shifted or rotated back into the column of material, returning it the flow of product for further disposition in the spray drying system. Thus, instead of having an outlet 150 located below the sampling compartment 14, the device of this embodiment includes a weighing surface of a scale positioned below the sampling compartment 14. The slice of material can rest on the weighing surface of the scale, and its weight measured in situ, without removing the material sample from the disc 120.

Figure 5:
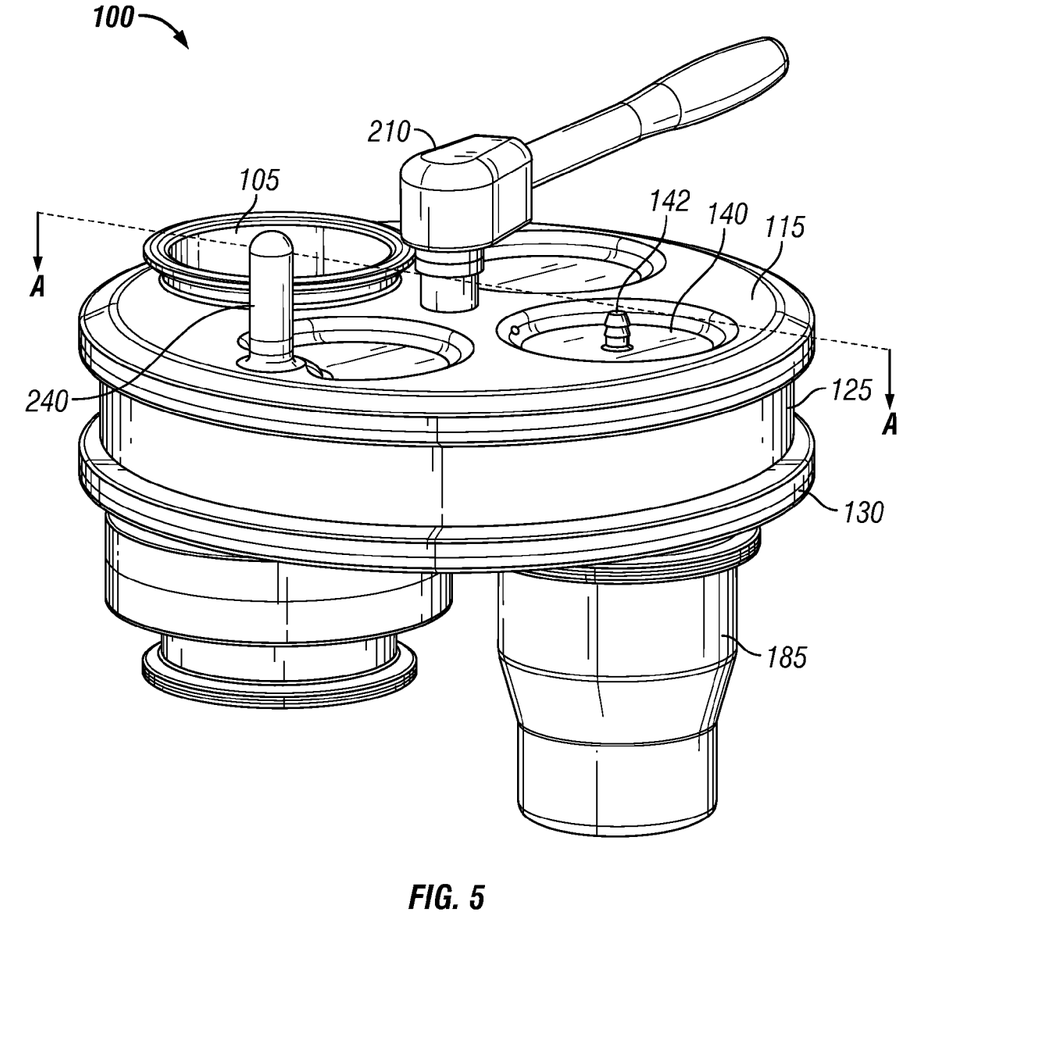
FIG. 5 is a perspective view of an embodiment of a device for inline sampling of a bulk material.

In one aspect, the weighing surface of the scale is flush with a top surface of the bottom plate 130 (FIG. 5). In another aspect, the sampling process is automated with motors and/or pneumatics, eliminating the need for an operator to collect and weigh the sample.

It can be seen that the devices described herein can include one or more of means for allowing a material to flow through a sampling compartment; means for closing off the flow of material below the sampling compartment; means for building up a column of material through the sampling compartment; means for shifting the sampling compartment to remove a slice of material in the column; and means for placing the slice of material into a sample container. Such devices have significant advantages over prior art sampling apparatus.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. A method of sampling a material, the method comprising:

flowing a material from a source to a bulk collection container along a flowpath;

allowing the material to flow through a first sampling compartment disposed in the flowpath between the source and the bulk collection container;

closing off the flow of material below the first sampling compartment;

building up a column of material through the first sampling compartment;

shifting the first sampling compartment to remove a slice of material in the column thereby placing a second sampling compartment in the flowpath between the source and the bulk collection container;

placing the slice of material into a sample container; and reopening the flow of material from the source to the bulk collection container through the second sampling compartment.

2. The method of claim 1, comprising weighing the slice of material to obtain a bulk density measurement.

3. The method of claim 1, wherein shifting the first sampling compartment reopens the flow of material through the second sampling compartment.

4. The method of claim 1, wherein removing the slice of material comprises removing a section of the column that represents substantially the entire cross-sectional flow of the material through the first sampling compartment.

5. The method of claim 1, wherein shifting the first sampling compartment comprises rotating a disc comprising the first sampling compartment through the flow of material.

6. The method of claim 5, wherein rotating the disc comprises rotating the disc 180°.

7. A device for sampling a material, the device comprising:
   means for flowing a material from a source to a bulk collection container along a flowpath;
   means for allowing a material to flow through a first sampling compartment disposed in the flowpath between the source and the bulk collection container;
   means for closing off the flow of material below the first sampling compartment;
   means for building up a column of material through the first sampling compartment;
   means for shifting the first sampling compartment to remove a slice of material in the column thereby placing a second sampling compartment in the flowpath between the source and the bulk collection container;
   means for placing the slice of material into a sample container; and
   means for reopening flow from the source to the bulk collection container through the second sampling compartment.

* * * * *